United States Patent [19]

Henkin et al.

[11] B 3,995,031

[45] Nov. 30, 1976

[54] METHOD OF CONTROLLING OBESITY WITH PURIFIED ACTIVE PRINCIPLE OF FRUIT OF *SYNSEPALUM DULCIFICUM*

[75] Inventors: Robert I. Henkin, Bethesda, Md.; Eugene L. Giroux, Strasbourg, France

[73] Assignee: The United States of America as represented by the Department of Health, Education and Welfare, Washington, D.C.

[22] Filed: July 23, 1974

[21] Appl. No.: 490,995

[44] Published under the second Trial Voluntary Protest Program on February 3, 1976 as document No. B 490,995.

Related U.S. Application Data

[62] Division of Ser. No. 354,098, April 24, 1973.

[52] U.S. Cl. .................................. 424/177; 424/195
[51] Int. Cl.² ................... A61K 37/00; A61K 35/78
[58] Field of Search ............. 424/177, 195; 426/217

[56] References Cited
OTHER PUBLICATIONS

Kurihara et al.–Chem. Abst. vol. 75 (1971) p. 1359j.

*Primary Examiner*—Sam Rosen
*Attorney, Agent, or Firm*—Holman & Stern

[57] ABSTRACT

A process for the purification of the active principle of the fruit of the plant *Synsepalum dulcificum* is disclosed. The process includes contacting the fruit with a suspension of polyvinyl pyrrolidone, followed by adsorption of the active principle by means of chromatography procedures. By following the process in accordance with the present invention, proteases and tannins are substantially completely eliminated from the final product. The active principle of this fruit, when prepared in accordance with the present invention, has been found to be particularly useful in controlling obesity in human beings.

1 Claim, No Drawings

METHOD OF CONTROLLING OBESITY WITH PURIFIED ACTIVE PRINCIPLE OF FRUIT OF SYNSEPALUM DULCIFICUM

This is a divisional of application Ser. No. 354,098, filed Apr. 24, 1973.

BACKGROUND AND SUMMARY OF THE INVENTION

The present invention relates to a process for purification of the active principle of the fruit of the plant *Synsepalum dulcificum*. Also disclosed is a method for the use of this active principle in the control of obesity.

The botanical plant species of *Synsepalum dulcificum* is indigenous to tropical West Africa, where it is often referred to as "miracle fruit." The plant, which grows in the form of a shrub, yields ripe red berries from December to June, the berries being ellipsoidal in shape and about 0.75 inch long, and composed of a thin layer of pulp surrounding a single large seed. These berries have the unique property of modifying the taste of sour foods to make such foods taste sweet after the fruit pulp has been chewed.

Previous methods for the purification of the active principle of plants such as *Synsepalum dulcificum* have been characterized by a complex series of steps involving bulky equipment and long periods of time for the separation of an active principle which in many cases has been of a low degree of purity, often containing contaminants such as proteases and tannins in relatively large amounts. Such prior art methods include those described by Inglett et al., *J. Agri. Food Chem.*, 13:284 (1965), Brouwer et al., *Nature* 220:373 (1968) and Beidler et al., *Science* 161:1241 (1968). The method of Inglett et al. involves purification of the active principle of miracle fruit in phases A and B, with phase A involving successive treatment of the plant parts with petroleum ether, chloroform, ethyl acetate, acetone, absolute ethanol and water, and phase B including successive treatment with water, aqueous alcohol, absolute alcohol, acetone, chloroform and n-hexane, followed by hydrolysis of fractions A and B. By removal of inactive matter, a five-fold concentration of the active material was achieved.

Brouwer et al. purified the active principle by ammonium sulfate fractionation and gel chromatography of the crude extract while Beidler et al. passed the crude extract through a column of diethylaminoethyl-Sephadex followed by ion-exchange chromatography on a carboxymethyl-Sephadex column.

By the present invention, there is provided a process for the purification of the active principle of the fruit of the plant *Synsepalum dulcificum* which is simple in nature and capable of being carried out in a short period of time to provide a product having a high degree of purity. The present method is accomplished with fewer steps than prior art processes and proteases and tannins are substantially completely eliminated. The presence of such contaminants in prior purification methods has resulted in destruction of the active principle by a process of enzymatic degradation and is a chief reason for the approximately two-fold increase in the activity of the principle prepared by the method of the present invention as compared with prior methods.

In general, an extract containing the desired active principle is obtained by extraction in a basic medium with polyvinyl pyrrolidone. The concentrated extract is acidified after addition of $\epsilon$-amino caproic acid with glacial acetic acid. The filtered solution containing the active principle is chromatographed on a carboxymethyl polyacrylamide gel adsorbent, employing liquid column chromatography techniques, following which the active principle is eluted with sodium phosphate. The active principle is then placed on a column of QAE-Sephadex A-50, an ion exchange medium of diethyl-(2-hydroxypropyl) aminoethyl groups coupled to a modified dextran matrix. The purpose of this step is to purify further the active principle by placing it through a cellulose or polyacrylamide-based strongly basic anion exchanger. The active principle is eluted from the column and may then be subjected to a third liquid column chromatography procedure on a column of carboxymethyl polyacrylamide gel. The active principle is again eluted with sodium phosphate to provide the final purified product.

It has been found that this active principle, prepared in accordance with the present invention, is very useful in controlling obesity when administered orally. Various pharmacological studies have been performed using the active principle of *Synsepalum dulcificum* as obtained by the present invention and through these studies the preferred and safe dosage levels have been determined. The active principle, often called "MFP" (miracle fruit principle) or "miraculin", is effective in controlling obesity at concentrations of $10^{-7}$ M.

DESCRIPTION OF THE PREFERRED EMBODIMENTS

The method of the present invention is more particularly described in accordance with the following specific embodiment:

Berries of the plant *Synsepalum dulcificum*, including pulp and skin, were allowed to soak for several hours at 0°–4°C. with stirring in a suspension of 1/5 part insoluble polyvinyl pyrrolidone (PVP) in 10 parts 0.1 M $Na_2CO_3$ buffer, pH 10.5. The soaking time can vary from about 4 hours to as long as overnight. The pH of the initial suspension is preferably in the range of about 10 to 11. Complete solubilization of the crude extract was found to occur only above the isoelectric point of the active principle, i.e., above pH 9. The quantities of the various components employed herein can, of course, be varied, depending upon the amount of raw material to be processed. The homogenate was filtered in the cold (4°C.). The supernatant contained the active principle as determined by bioassay. A typical yield was 40 mg. of trichloroacetic acid (TCA)-precipitable nitrogen per 100 gm wet weight of berries. The supernatant was then made 0.1 M with respect to $\epsilon$-amino caproic acid and additional insoluble PVP was added, the amount of additional PVP preferably being equivalent to the amount employed in the initial suspension. Over an ½ hour period glacial acetic acid was added dropwise to the stirred suspension at 0°–4°C. to lower the pH to 6.0–6.5. Other equivalent acids may be employed in this step, other than glacial acetic acid. After filtration, a solution containing the active principle, determined by bioassay, was obtained, a typical yield being 20 mg. of TCA-precipitable nitrogen per 100 gm wet weight of berries. The active principle was then adsorbed onto a short column of BioGel-CM-30 resin, a trade name for a support material containing sodium carboxymethyl groups covalently linked to a polyacrylamide matrix, equilibrated with 0.1 M $NaH_2PO_4$ buffer, pH 6.0, at 0°–4°C. The column was next washed with 0.1 M buffer, pH 6.5, then the active principle was eluted stepwise with 0.1 M $Na_2HPO_4$. A typical yield was 5 mg of TCA-precipitable nitrogen per 100 gm wet berry weight. The active principle was adjusted to pH 10.5 by addition of 0.1 N NaOH in 2% sodium carbonate. QAE Sephadex A-50 resin sufficient to form a 150 ml column was equilibrated with 0.1 M sodium carbonate buffer, pH 10.5. Half of the resin was added to the solution of active principle and the slurry was poured onto a 2.5 cm. diameter column formed from the other portion of resin. After packing, the column was washed with one column volume of 0.05 M NaCl in 0.1 M sodium carbonate buffer, pH 10.5. Elution was effected by a linear gradient of 0.05 to 0.65 M NaCl in 0.1 M sodium carbonate buffer, pH 10.5.

The active principle was concentrated and solvent was exchanged for 0.1 M sodium phosphate buffer, pH 6.0. The concentrate was pumped onto a 2.5 × 20 cm column of carboxymethyl polyacrylamide gel. A shallow pH gradient in $Na_2HPO_4$ buffer eluted the active principle over the pH range 7.0–7.3. A typical overall yield was 20–25 mg. of protein per 100 gm wet weight of berries. An overall recovery of one-fifth of the taste changing activity present in the crude extract was observed. This represents a three-fold increase in specific activity. Other equivalent support materials may be employed in these chromatographic steps, the herein described gel supports having been found to provide particularly good results.

In the use of the active principle of the fruit of *Synsepalum dulcificum* to control obesity, it has been found that the active principle can be administered orally with good results. For the human adult an oral dosage of about 10 to 400 μg. has been found to be quite effective. In particular, to provide the desired effect over a time period of 10 to 30 minutes, the length of time required to consume a short meal, about 10 to 100 μg. of the purified principle may be administered to a human adult. To produce the desired effect over longer periods of time, say 1 to 3 hours, about 100 to 400 μg. should be employed. These dosages may be administered as frequently as 5 times a day without adverse effect. Upon being administered orally, the active principle should be held in the mouth for at least two minutes and then either expectorated or swallowed. A sweetening effect is thereafter observed for the time intervals as stated above.

In controlling obesity by the use of the active principle which has been prepared in accordance with the present invention, a non-metabolic agent such as methyl cellulose or other equivalent substance should preferably be provided for consumption by the subject whose weight is to be controlled. Dilute acid such as hydrochloric, citric or the like is preferably administered along with the non-metabolic agent. By administering the active principle prior to consumption of the non-metabolic preparation, the non-metabolic preparation will be found to taste satisfyingly sweet so that the appetite of the individual is substantially satisfied although caloric intake is minimized. Such dosages of the active principle have been found to prevent the gaining of weight in normal human adults because the non-metabolic foodstuffs presented contained little or no caloric value although the foodstuffs were determined to be satisfyingly sweet and filling. The decreased caloric intake thus results in a corresponding weight loss.

The active principle of *Synsepalum dulcificum* has been administered to approximately 30 normal human volunteers in the dosages as previously described without any ill effect. The active principle has also been used by the natives in Western Africa, Nigeria, Ghana and Guinea for extended periods of time without any known ill effect.

The active principle of the fruit of *Synsepalum dulcificum* may be employed directly in the form as obtained by the purification method outlined herein. The active principle may also be formulated into pharmaceutical compositions comprising a carrier such as methyl cellulose and the active principle in an amount sufficient to control obesity. The pharmaceutical carrier employed in these compositions may be either solid or liquid, and the active principle may also be administered in either the solid or liquid form. These compositions can be prepared containing exact amounts of the active principle by virtue of its pure state of preparation according to the present invention. The uniformity and standardization of the desired obesity controlling effects produced by the active principle as purified herein is not possible with either the whole plant material of *Synsepalum dulcificum* or crude extracts thereof.

Having thus described the present invention, it is apparent that certain modifications and variations can be made without departing from the spirit and scope of the invention, or sacrificing its attendant advantages, the forms hereinbefore described being merely the preferred embodiments thereof.

It is claimed:

1. A method of controlling obesity which comprises orally administering to a human from about 10 to 400 μg. of the taste-modifying active principle of the fruit of the plant *Synsepalum dulcificum* and maintaining said active principle in the human's mouth for at least about 2 minutes, thereby providing a sweetening effect in the human's mouth lasting for a controlled time period of from about 10 minutes to about 3 hours depending upon the specific dosage administered, said sweetening effect being such that low-caloric value foodstuffs containing acids subsequently ingested by the human during said time period will taste satisfyingly sweet, said active principle having been obtained by the steps of:
  a. contacting the fruit of *Synsepalum dulcificum* with a suspension of polyvinyl pyrrolidone in a basic medium;
  b. filtering the suspension to obtain a supernatant containing the active principle of the fruit;
  c. adding ε-amino caproic acid to the supernatant;
  d. acidifying the supernatant to reduce the pH to the range of 6.0 – 6.5;
  e. filtering the supernatant to obtain a solution of the active principle;
  f. adsorbing the active principle on at least one chromatographic column, with at least one column employing a support material selected from the group consisting of cellulose and polyacrylamide-based strongly basic anion exchangers; and
  g. eluting the active principle with $Na_2HPO_4$ to recover the active principle from the column.

* * * * *